(12) United States Patent
Kim et al.

(10) Patent No.: US 10,850,282 B2
(45) Date of Patent: Dec. 1, 2020

(54) MULTIPLEX PCR CHIP AND MULTIPLEX PCR DEVICE COMPRISING SAME

(71) Applicant: NANOBIOSYS INC., Seoul (KR)

(72) Inventors: Sung Woo Kim, Seoul (KR); Duck Joong Kim, Anyang-si (KR); Seung Hyun Jeun, Seoul (KR)

(73) Assignee: NANOBIOSYS INC., Seoul (KR)

(*) Notice: Subject to any disclaimer, the term of this patent is extended or adjusted under 35 U.S.C. 154(b) by 104 days.

(21) Appl. No.: 15/327,300

(22) PCT Filed: Jun. 22, 2015

(86) PCT No.: PCT/KR2015/006322
§ 371 (c)(1),
(2) Date: Jan. 18, 2017

(87) PCT Pub. No.: WO2016/013770
PCT Pub. Date: Jan. 28, 2016

(65) Prior Publication Data
US 2017/0151571 A1    Jun. 1, 2017

(30) Foreign Application Priority Data

Jul. 23, 2014 (KR) .......... 10-2014-0093312

(51) Int. Cl.
*B01L 7/00* (2006.01)
*C12M 1/38* (2006.01)
(Continued)

(52) U.S. Cl.
CPC .............. *B01L 7/52* (2013.01); *C12M 1/38* (2013.01); *C12M 23/12* (2013.01); *C12M 23/22* (2013.01);
(Continued)

(58) Field of Classification Search
CPC ..... B01L 2200/0684; B01L 2200/0689; B01L 2300/0654; B01L 2300/0816;
(Continued)

(56) References Cited

U.S. PATENT DOCUMENTS

2003/0190608 A1   10/2003   Blackburn
2005/0161669 A1*   7/2005   Jovanovich ....... B01L 3/502715
                                                    257/48
(Continued)

FOREIGN PATENT DOCUMENTS

CN   102985527 A   3/2013
CN   103517991 A   1/2014
(Continued)

*Primary Examiner* — Gautam Prakash
*Assistant Examiner* — Lydia Edwards
(74) *Attorney, Agent, or Firm* — Novick, Kim & Lee, PLLC; Sang Ho Lee

(57) ABSTRACT

According to one embodiment of the present invention, a multiplex PCR device is disclosed. The multiplex PCR device comprises a multiplex PCR chip simultaneously carrying a plurality of mutually different nucleic acid molecules, and the invention may be characterised in that, attached spaced apart from each other on the multiplex PCR chip, there are a plurality of probes used for hybridization reactions whereby hybridization takes place specifically with mutually different amplified sequences of the nucleic acid molecules.

12 Claims, 13 Drawing Sheets

(51) Int. Cl.
*C12M 1/32* (2006.01)
*C12M 1/00* (2006.01)
*B01L 99/00* (2010.01)
*C12M 1/02* (2006.01)

(52) U.S. Cl.
CPC ............ *C12M 31/00* (2013.01); *C12M 41/18* (2013.01); *B01L 2200/0684* (2013.01); *B01L 2200/0689* (2013.01); *B01L 2300/0654* (2013.01); *B01L 2300/0816* (2013.01); *B01L 2300/16* (2013.01); *B01L 2300/1805* (2013.01)

(58) Field of Classification Search
CPC ......... B01L 2300/16; B01L 2300/1805; B01L 7/52; C12M 23/12; C12M 23/22; C12M 31/00; C12M 41/18
See application file for complete search history.

(56) References Cited

U.S. PATENT DOCUMENTS

| | | | | |
|---|---|---|---|---|
| 2008/0220420 A1* | 9/2008 | Nakamura | ............ | B01L 3/5027 435/6.11 |
| 2009/0011943 A1* | 1/2009 | Drmanac | ............... | C12N 15/64 506/4 |
| 2012/0141999 A1* | 6/2012 | Park | .................. | B01L 3/502715 435/6.12 |
| 2013/0288916 A1* | 10/2013 | Alexandre | ........ | B01L 3/502784 506/9 |
| 2014/0179566 A1 | 6/2014 | Linton et al. | | |

FOREIGN PATENT DOCUMENTS

| | | |
|---|---|---|
| EP | 2138232 A1 | 12/2009 |
| JP | 2005-140652 A | 6/2005 |
| JP | 2006-271216 A | 10/2006 |
| JP | 2006-345813 A | 12/2006 |
| JP | 2006-345816 A | 12/2006 |
| JP | 2008-278810 A | 11/2008 |
| JP | 2009-544016 A | 12/2009 |
| JP | 2012-509078 A | 4/2012 |
| JP | 50-89092 B2 | 12/2012 |
| JP | 2013-007592 A | 1/2013 |
| JP | 2013-524808 A | 6/2013 |
| KR | 10-2011-0118572 A | 10/2011 |
| KR | 10-2014-0028431 A | 3/2014 |
| KR | 10-2014-0029627 A | 3/2014 |
| WO | 2012/108499 A1 | 8/2012 |
| WO | 2012/151192 A2 | 11/2012 |
| WO | 2013/180406 A1 | 12/2013 |
| WO | 2014/028061 A1 | 2/2014 |

\* cited by examiner (a)

(b)

MULTIPLEX PCR CHIP AND MULTIPLEX PCR DEVICE COMPRISING SAME

TECHNICAL FIELD

The present invention relates to a multiplex PCR chip and a multiplex PCR device including the same, and more specifically, to a multiplex PCR chip for simultaneously detecting a plurality of nucleic acid molecules different from each other based on positions of a plurality of probes and a multiplex PCR device including the same.

The present invention has been derived from a research sponsored by Health medical technology research development project of Korea Health Industry Development Institute of Ministry of Health and Welfare [Project number: HI13C2262, Project name: "Development of Real-time PCR system automating entire process of multi-channel simultaneous multi-detection based on a lab-on-a-chip for high-speed diagnosis of genes for field test of malaria"].

BACKGROUND ART

Polymerase Chain Reaction (PCR) is a technique of repeatedly heating and cooling a sample solution containing nucleic acids to successively replicate a portion having a specific base sequence of a nucleic acid and exponentially amplifying the nucleic acid having the portion of the specific base sequence, and specifically, it may be progressed to a series of temperature enzyme reaction steps including denaturation, annealing, extension and the like. The PCR is widely used in life science, genetic engineering, medical field and the like for analysis and diagnosis purposes.

Meanwhile, a technique of diagnosing through amplification of a nucleic acid as described above or searching for a specific gene is limited because only one template is searched at a time. It is work-troublesome and time-consuming to amplify one template at a time when it needs to amplify several templates. For example, even if the same symptoms occur in the same patient, the cause of the onset is often due to various types of infectious agents, and individual diagnosis of various pathogens is needed. In addition, it is known that cancers or genetic defects are caused by composite variations of various genes. Since polymorphism or mutation of a gene is caused by diverse changes of loci of the gene, test of additional zygotes is required. Since the amount of a nucleic acid that can be extracted from a limited sample is limited in a general environment, repetitive diagnosis cannot be performed through amplification of a nucleic acid using a limited amount of the nucleic acid in many cases.

Accordingly, a technique of simultaneously analyzing nucleic acids of many templates from the same sample is needed, and such an analysis technique may be referred to as multiplex PCR. In relation to this, FIG. 1 shows an exemplary process of multiplex PCR of the prior art.

Referring to FIG. 1, a conventional multiplex PCR may perform a PCR reaction by injecting multiple types of primer sets into one reaction container (or tube). The multiple types of primer sets may be specifically hybridized with various sequences of nucleic acid molecules, and accordingly, a plurality of target nucleic acid sequences may be simultaneously amplified. That is, the multiplex PCR may confirm/diagnose a plurality of genes and diseases in one experiment and therefore may reduce the number of experiments and labor and provide an effect of cost reduction.

However, special detection equipment is required to monitor an amplification product of the multiplex PCR in real-time and this may increase the overall size and complexity of a PCR device and result in cost non-effectiveness. Specifically, monitoring the amplification product of the multiplex PCR may be performed by radiating excitation light and detecting emission light generated therefrom while the amplification reaction is progressed, and here, an oligonucleotide (i.e., a primer or a probe) marked by a fluorescent dye capable of generating a signal indicating existence of a target nucleic acid sequence during the amplification reaction is used to generate the emission light, and particularly, in the multiplex PCR, various oligonucleotides specific to each nucleic acid sequence can be used to distinguish a plurality of diverse nucleic acid sequences that can be amplified. That is, in the conventional multiplex PCR, multiple types of fluorescent dyes should be marked to detect multiple types of target nucleic acid sequences, and in addition, a light source and a filter of multiple wavelengths, which are optimized for detection of each fluorescent dye in a separate wavelength band, are required to detect multiple types of emission light from the multiple types of fluorescent dyes. This may increase the time consumed for detecting a nucleic acid sequence since a measurement time is needed for each of the multiple wavelengths, increase the overall size and complexity of the PCR device, and result in cost non-effectiveness.

Accordingly, a multiplex PCR device of a simple overall structure, which can minimize the total PCR reaction time and obtain a reliable PCR reaction throughput, is required.

DISCLOSURE OF INVENTION

Technical Problem

Therefore, the present invention has been made in view of the above problems, and it is an object of the present invention to provide a multiplex PCR device for simultaneously detecting a plurality of nucleic acid molecules different from each other based on positions of a plurality of probes.

Technical Solution

According to an embodiment of the present invention, a multiplex PCR chip is disclosed. The multiplex PCR chip includes a plurality of probes for hybridization reaction, specifically hybridized with different amplified sequences of a plurality of nucleic acid molecules different from each other in order to simultaneously detect the nucleic acid molecules, in which the plurality of probes is fixed to be space apart from each other.

According to an embodiment of the present invention, a multiplex PCR device is disclosed. The multiplex PCR device may include: the multiplex PCR chip; a light providing part for radiating excitation light toward the probes in the multiplex PCR chip; and a light detection part for detecting emission light generated from a plurality of probes by the excitation light, in which detection by the light providing part and the light detection part is performed using light of a single wavelength.

According to an embodiment of the present invention, a multiplex PCR device is disclosed. The multiplex PCR device may include the multiplex PCR chip and at least one heat block contacting with the multiplex PCR chip to transfer heat for multiplex PCR to the multiplex PCR chip.

Advantageous Effects

According to the present invention, since sequences of nucleic acid molecules hybridized by probes can be distinguished based on positions of the probes by arranging multiple types of probes specifically hybridized with the sequences of nucleic acid molecules different from each other, necessity of different fluorescent dyes for marking the probes can be removed.

According to the present invention, since sequences of nucleic acid molecules hybridized with probes can be distinguished based on positions of the probes, a multiplex PCR product can be detected using only one type of light source and filter. This may miniaturize optical equipment and reduce the cost of the equipment and, furthermore, improve efficiency of operation of the multiplex PCR device, such as reducing the time consumed for detection.

According to the present invention, since multiple types of probes are bonded on the surface of the multiplex PCR chip through a certain adhesive material, a further stronger bonding force may be provided, and this may prevent a distorted result generated during separation of bonding, hybridization and cleansing.

According to the present invention, since the adhesive material may form a pore structure and the probes are bonded on the surface of the pore structure, the contact area between the probes and the multiplex PCR product is increased, and thus reactivity can be improved.

BRIEF DESCRIPTION OF THE DRAWINGS

Brief description on each drawing is provided to further understand the drawings referenced in the detailed description of the present invention.

DESCRIPTION OF SYMBOLS

Figure 1:
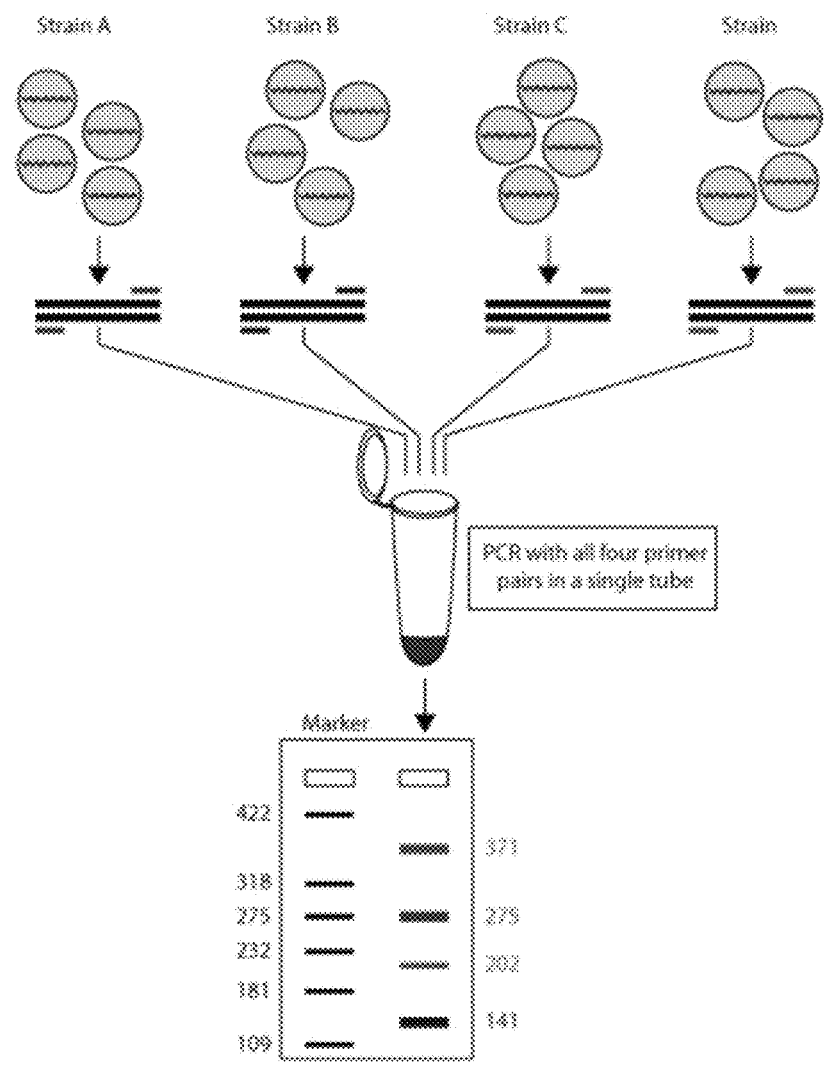
FIG. 1 shows an exemplary process of multiplex PCR of the prior art.

Best Mode for Carrying Out the Invention

Hereafter, embodiments according to the present invention will be described with reference to the accompanying drawings. In assigning reference numerals to constitutional components of each drawing, it should be noted that like constitutional components will have like reference numerals if possible although they are shown in different drawings. In addition, in describing the embodiments of the present invention, if specific description of already known constitution or functions related to the present invention may hinder understanding of the present invention, detailed description thereof will be omitted. In addition, although the embodiments of the present invention will be described hereinafter, the technical spirits of the present invention will not be limited or restricted thereto and may be modified by those skilled in the art and diversely embodied.

Throughout the specification, when an element is connected to another element, it includes a case of indirectly connecting the elements with intervention of another element therebetween, as well as a case of directly connecting the elements. In addition, the concept of including a constitutional element means further including another constitutional element, not excluding another constitutional element, as far as an opposed description is not specially specified.

A multiplex PCR device according to the present invention is a device for performing multiplex polymerase chain reaction (PCR) for amplifying various nucleic acids having a specific base sequence. Specifically, to amplify a DNA (a deoxyribonucleic acid) having a specific base sequence, the multiplex PCR device performs a denaturing step of separating a double-stranded DNA to single-stranded DNAs by heating a sample solution containing the double-stranded DNA at a specific temperature of, for example, about 95° C., an annealing step of forming a partial DNA-primer complex by providing the sample solution with an oligonucleotide primer having a sequence complementary to a specific base sequence to be amplified, and bonding the primer to the specific base sequence of the single-stranded DNA by cooling down the primer together with a separated single-stranded DNA at a specific temperature of, for example, 55° C., and an extension (amplification) step of forming a double-stranded DNA based on the primer of the partial DNA-primer complex by DNA polymerase by maintaining an appropriate temperature, e.g., 72° C., of the sample solution after the annealing step, and the DNA having a specific base sequence may be exponentially amplified by repeating the three steps, for example, twenty to forty times. Further, in some cases, the PCR device may simultaneously perform the annealing step and the extension (amplification) step, and in this case, the PCR device may complete a first cycle by performing two steps configured of the extension step and the annealing and extension (amplification) step. Accordingly, the multiplex PCR device according to an embodiment of the present invention refers to a device including modules for performing these steps, and it is assumed that details of the modules, which are not disclosed in this specification, are disclosed in the conventional technique for performing PCR, and all the modules are provided if it is apparent that they are needed.

In addition, the multiplex PCR device may measure whether a multiplex PCR product is generated and analyze a degree of the generation in real-time while performing multiplex PCR. A fluorescent material, as well as a reagent needed for the PCR reaction, is added to the multiplex PCR chip, and an optical signal that can be measured and analyzed is induced as the fluorescent material emits light by the light of a specific wavelength according to generation of the PCR product.

Figure 2:
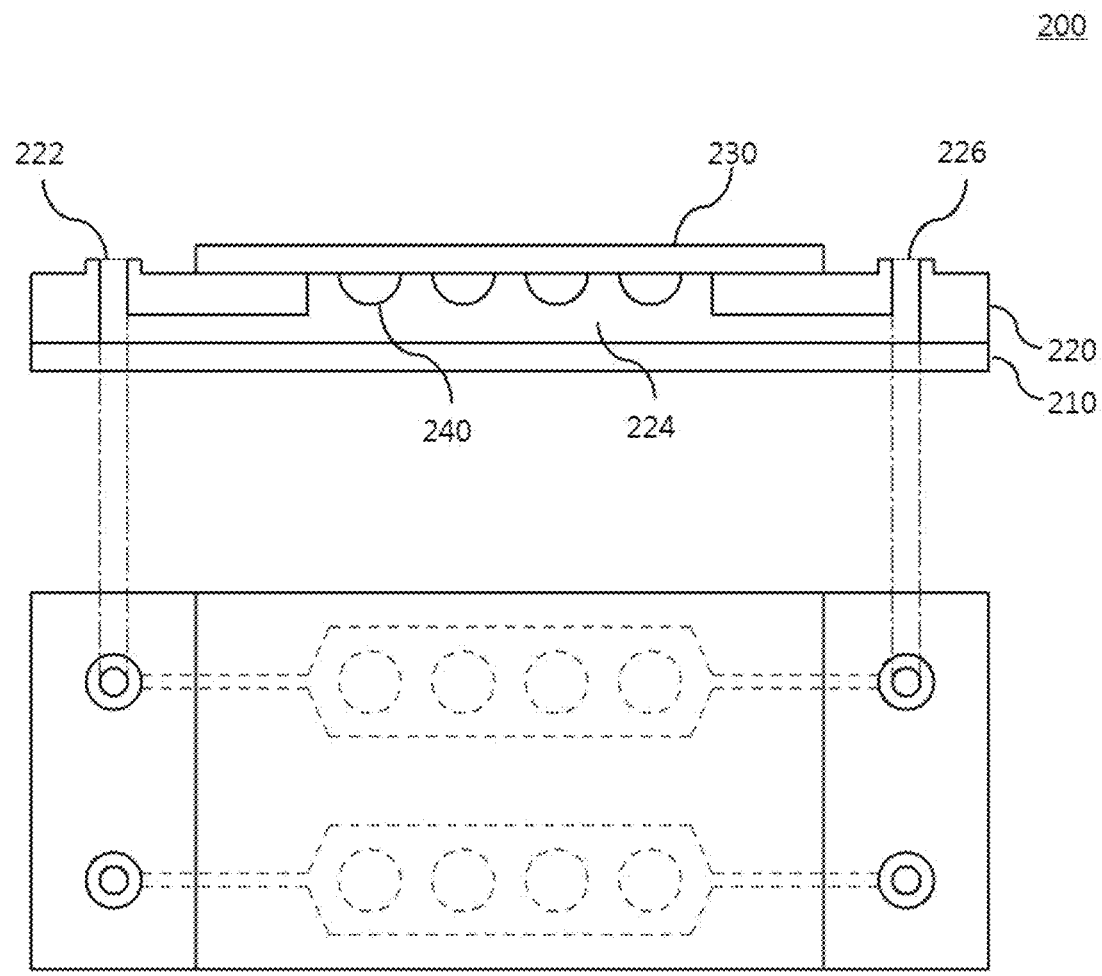
FIG. 2 shows a multiplex PCR chip according to an embodiment of the present invention.

FIG. 2 shows a multiplex PCR chip according to an embodiment of the present invention.

Referring to FIG. 2, a multiplex PCR chip 200 is an element for performing amplification of a nucleic acid molecule (amplification reaction), detection of a target sequence (hybridization reaction) and the like and may include one or more reaction areas 224 for accommodating fluid. Here, the fluid may be a sample solution including a nucleic acid, e.g., a double-stranded DNA, an oligonucleotide primer having a sequence complementary to a specific base sequence to be amplified, a DNA polymerase, deoxyribonucleotide triphosphates (dNTP), a PCR reaction buffer and the like.

At least a portion of the multiplex PCR chip 200 may be implemented using a light transmissive material, and the light transmissive material preferably includes a light transmissive plastic material. Since the multiplex PCR chip 200 uses a plastic material, it may enhance heat transfer efficiency by adjusting only the thickness of the plastic, and manufacturing cost may be reduced since the manufacturing process is simple. In addition, since the multiplex PCR chip 200 may be provided with a light transmissive property overall, light may be directly radiated while the multiplex PCR chip 200 is arranged on one side of a heat block, and thus whether a nucleic acid is amplified and a degree of the amplification can be measured and analyzed in real-time. If the multiplex PCR chip 200 contacts with the heat block for amplification reaction, the heat of the heat block is transferred to the multiplex PCR chip 200, and the fluid contained in the reaction area 224 of the multiplex PCR chip 200 is heated up or cooled down, and thus a constant temperature can be maintained. Although the multiplex PCR chip 200 may have a shape of a flat surface overall, the multiplex PCR chip is not limited thereto.

As shown in FIG. 2, the multiplex PCR chip 200 may include probes 240 fixed therein for hybridization reaction. The probes 240 are marked as oligonucleotides, which may generate a signal indicating existence of a target nucleic acid sequence during the amplification reaction to detect a nucleic acid amplified through the PCR and can be specifically hybridized with the amplified sequences of the nucleic acid molecules. Each of the probes 240 may be hybridized with a different amplified sequence of a nucleic acid molecule.

The probes 240 may be bonded on the surface of the multiplex PCR chip 200 to be spaced apart from each other. Such a bonding may be performed by applying the probes 240 on the surface of the multiplex PCR chip 200 using, for example, a spotter, an arrayer, ink-jet or the like. According to embodiments, each of the probes 240 may be bonded on the surface of the multiplex PCR chip 200 through covalent bonding or using an adhesive material. Here, the adhesive material may be at least one of hydrogel, agarose and paraffin. These adhesive materials may provide a further stronger bonding force, compared with the covalent bonding of the prior art, between the probes 240 and the multiplex PCR chip 200, and this may prevent a distorted result generated during separation of bonding, hybridization and cleansing. In addition, the adhesive materials may form a pore structure, and as the probes 240 are bonded on the surface of the pore structure, the contact area between the probes 240 and the multiplex PCR product (i.e., an amplified nucleic acid molecule) is increased, and thus reactivity can be improved. In addition, the probes 240 may be arranged on the top surface of the reaction area 224 (or on the top inner surface of the multiplex PCR chip 200 or on the bottom surface of a third plate 230). Bubbles may be generated during the PCR reaction, and although the bubbles may generate interference in measuring a PCR reaction product, since the probes 240 are arranged on the top surface of the reaction area 224 as shown in FIG. 2, the bubbles are moved around the probes 240, and the interference is removed, and thus efficiency of measurement can be improved.

The same fluorescent dye may be used for a plurality of probes 240. Probes 240 marked by fluorescent dyes having colors different from each other should be used in the multiplex PCR of the prior art to distinguish sequences of nucleic acid molecules hybridized by a plurality of probes 240. However, in the present invention, although the same fluorescent dye is used, a plurality of probes 240 is arranged to be spaced apart from each other by a predetermined distance, and accordingly, sequences of nucleic acid molecules hybridized by the probes 240 can be distinguished based on positions of the probes, and thus necessity of different fluorescent dyes can be removed.

Use of the same fluorescent dye like this may simplify an optical device for detecting emission light using a fluorescent dye. In the conventional multiplex PCR, a plurality of different probes 240 that can be specifically hybridized with amplified sequences of nucleic acid molecules in one reaction container is marked by different fluorescent dyes, and an optical device having a plurality of wavelengths specific to each fluorescent dye is used to distinguish emission light by the fluorescent dyes. However, in the present invention, although emission light by the same dyeing sample, i.e., emission light of the same color, is generated by radiating excitation light having one wavelength toward multiple types of probes 240, sequences of the amplified nucleic acid molecules can be distinguished based on positions of the probes 240. That is, in the present invention, a multiplex PCR product can be detected using only one type of light source and filter, and this may miniaturize optical equipment and reduce the cost of the equipment and, furthermore, improve efficiency of operation of the multiplex PCR device, such as reducing the time consumed for detection.

Describing the structure of the multiplex PCR chip 200 shown in FIG. 2 in more detail, a first plate 210 of a plate shape may be provided as a base of the multiplex PCR chip 200. A second plate 220 and a third plate 230 may be sequentially arranged on the first plate 210. Although the first plate 210 may be implemented using various materials, preferably, it may be implemented using a thermoplastic resin material or a thermosetting resin material selected from a group configured of polymethylmethacrylate (PMMA), polycarbonate (PC), cycloolefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA) and a combination thereof.

The second plate 220 may be arranged on the first plate 210. The second plate 220 may include an inflow part 222 through which a fluid (e.g., a sample solution or the like containing a nucleic acid to be amplified) flows in, a reaction area 224 in which the flowed-in fluid moves and a PCR reaction and a hybridization reaction are performed, and an outflow part 226 through which the fluid flows out after the reactions are completed. As shown in the figure, the reaction area 224 of the second plate 220 may be formed to be depressed from the surface (e.g., the top surface and/or the bottom surface) of the second plate 220 or to penetrate the second plate 220. In addition, the inflow part 222 and the outflow part 226 of the second plate 220 may be formed to penetrate the second plate 220 and, at the same time, to be protruded from the surface of the second plate 220, which will be described below in more detail.

Although the second plate 220 may be implemented using various materials, preferably, it may be implemented using a material selected from a group configured of polydimethylsiloxane (PDMS), cycle olefin copolymer (COC), polymethylmetharcylate (PMMA), polycarbonate (PC), polypropylene carbonate (PPC), polyether sulfone (PES), polyethylene terephthalate (PET) and a combination thereof.

In addition, although thickness of the second plate 220 may be diverse, it can be selected from a range of 0.1 to 2.0 mm. In addition, although the width and length of the reaction area 224 may be diverse, preferably, the width of the reaction area 224 may be selected from a range of 0.5 to 3 mm, and the length of the reaction area 224 may be selected from a range of 20 to 60 mm. In addition, the inner wall of the second plate 220 may be coated with a material of a silane family, Bovine Serum Albumin (BSA) or the like to prevent adsorption of DNA or protein, and treatment of the material may be performed according to a method publicized in the art. In addition, although the inflow part 222 may be provided in a variety of sizes, preferably, its diameter may be selected from a range of 1.0 to 3.0 mm. In addition, although the outflow part may be provided in a variety of sizes, preferably, its diameter may be selected from a range of 1.0 to 3.0 mm.

The third plate 230 may be arranged on the second plate 220. Specifically, the third plate 230 is arranged on the second plate 220 to cover a partial area in the reaction area 224 of the second plate 220 (i.e., the penetrated area in the reaction area 224 of the second plate 220) and, at the same time, measure a PCR reaction product through at least one of the probes 240 arranged on a partial area on the bottom surface of the third plate 230 to be spaced apart from each other.

Although the third plate 230 may be implemented using various materials, preferably, it may be implemented using a material selected from a group configured of polydimethylsiloxane (PDMS), cycle olefin copolymer (COC), polymethylmetharcylate (PMMA), polycarbonate (PC), polypropylene carbonate (PPC), polyether sulfone (PES), polyethylene terephthalate (PET) and a combination thereof. In addition, although thickness of the third plate 230 may be diverse, preferably, the thickness may be selected from a range of 0.1 to 2.0 mm.

The shape of at least one of the first plate 210, the second plate 220 and the third plate 230 may be formed by various mechanical or chemical processes such as injection molding, hot-embossing, casting, laser ablation and the like. The processing methods are only exemplary, and various processing methods may be applied according to embodiments to which the present invention is applied. In addition, bonding between the first plate 210 and the second plate 220 and/or bonding between the second plate 220 and the third plate 230 may be performed by various bonding methods applicable in the art, such as thermal bonding, ultrasonic bonding, ultraviolet bonding, solvent bonding, tape bonding and the like.

According to embodiments, surface treatment may be performed on at least a portion of the inner surface of the multiplex PCR chip 200 (e.g., the inner wall of the second plate 220). For example, the surface may be coated with a material of a silane family, Bovine Serum Albumin (BSA) or the like to prevent adsorption of DNA or protein, and the surface treatment may be performed according to various techniques publicized in the art.

In addition, according to embodiments, the multiplex PCR chip 200 is provided with a separate cover means (not shown) for the inflow part 222 and/or the outflow part 226 to prevent contamination of the inside of the multiplex PCR chip 200 through the inflow part 222 and the outflow part 226 or to prevent leakage or the like of the fluid injected in the multiplex PCR chip 200. Such a cover means may be implemented in a variety of shapes, sizes or materials.

The shape or structure of the multiplex PCR chip 200 shown in FIG. 2 is only exemplary, and multiplex PCR chips of various shapes or structures may be used according to embodiments to which the present invention is applied.

Figure 3:
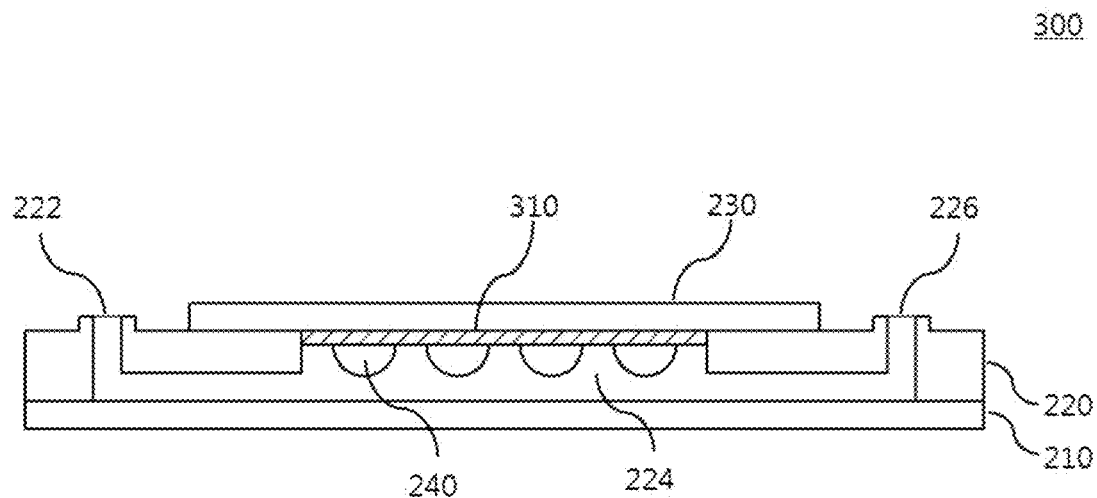
FIG. 3 shows a multiplex PCR device according to an embodiment of the present invention.

FIG. 3 shows a multiplex PCR device according to an embodiment of the present invention.

Referring to FIG. 3, a hydrophilic material 310 is processed on at least one area on the inner surface of a multiplex PCR chip 300 (i.e., an area on the bottom surface of the third plate 230) to smoothly perform multiplex PCR. Although the hydrophilic material 310 may be various materials, preferably, it may be a material selected from a group configured of a carboxyl group (—COOH), an amine group (—NH2), a hydroxyl group (—OH) and a sulfonic group (—SH). In addition, although the hydrophilic material 310 may be processed in a method selected from a group configured of an oxygen and argon plasma process, a corona discharge process and application of surfactant, this is only exemplary, and various processing methods publicized in the art may be applied according to embodiments to which the present invention is applied.

Figure 4:
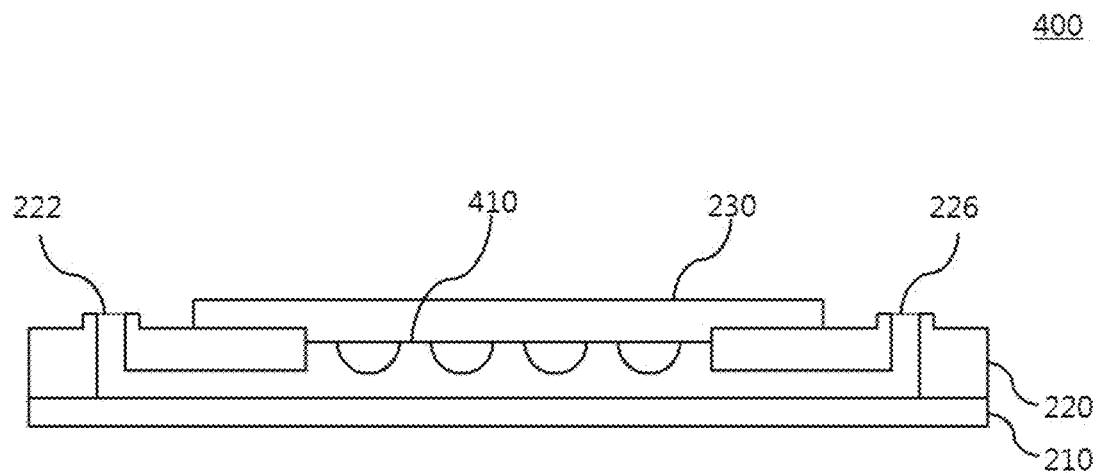
FIG. 4 shows a multiplex PCR chip according to an embodiment of the present invention.

FIG. 4 shows a multiplex PCR chip according to an embodiment of the present invention.

Referring to FIG. 4, in a multiplex chip 400, the third plate 230 may be arranged to be inserted into a partial area in the reaction area 224 of the second plate 220 (i.e., the penetrated area in the reaction area 224 of the second plate 220). To this end, a partial area 410 on the bottom surface of the third plate 230 may be formed to be protruded toward the bottom. The partial area 410 formed to be protruded like this may cover the penetrated area in the reaction area 224 of the second plate 220 and, at the same time, may easily accomplish bonding alignment of the third plate 230 and the second plate 220 through insertion into the penetrated area.

The shape of the multiplex PCR chip 400 shown in FIG. 4 is only exemplary, and various shapes may be applied according to embodiments to which the present invention is applied.

Figure 5:
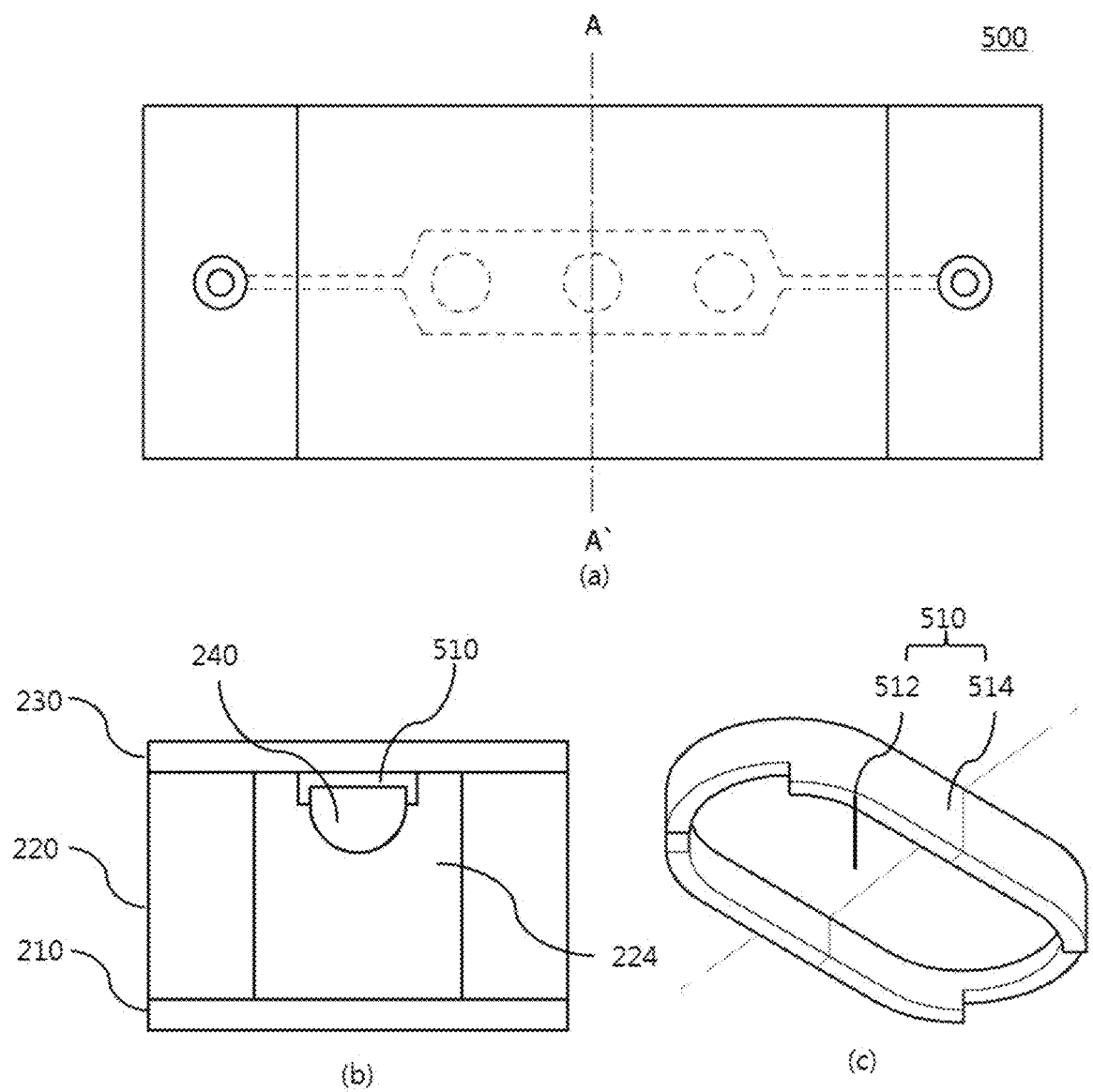
FIG. 5 shows a multiplex PCR chip according to an embodiment of the present invention.

FIG. 5 shows a multiplex PCR chip according to an embodiment of the present invention.

Specifically, FIG. 5(a) shows a plan view of a multiplex PCR chip 500, FIG. 5(b) shows a cross-sectional view of A-A' direction of the multiplex PCR chip 500, and FIG. 5(c) shows a perspective view of the inner bottom surface of the multiplex PCR chip 500 shown in FIGS. 5(a) and 5(b).

Referring to FIG. 5, the multiplex PCR chip 500 may further include a probe fixing part 510. The probe fixing part 510 is an element for accommodating and fixing the probes 240 for detection of a target sequence and may be configured of, for example, a center part 512 formed in an area on the bottom surface of the third plate 230 of the multiplex PCR chip 500 and a surrounding part 514 protruded to surround the center part 512. Here, the center part 512 may provide a space for accommodating the probes 240, and the surrounding part 514 may prevent departure of the probes 240 accommodated in the center part 512.

The shape of the probe fixing part 510 shown in FIG. 5 is only exemplary, and probe-fixing parts of various shapes may be used according to embodiments to which the present invention is applied.

Figure 6:
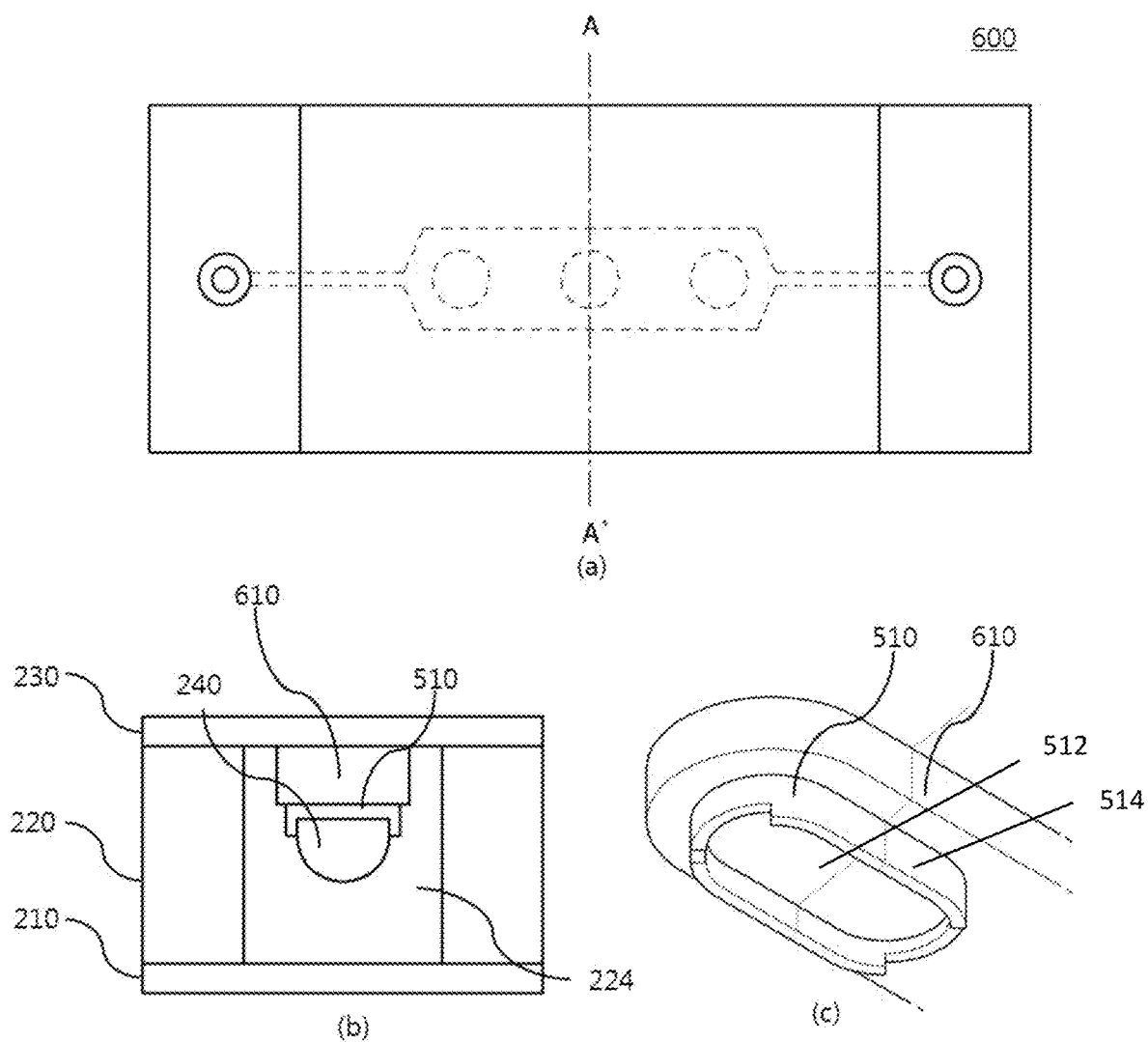
FIG. 6 shows a multiplex PCR device according to an embodiment of the present invention.

FIG. 6 shows a multiplex PCR device according to an embodiment of the present invention.

Specifically, FIG. 6(a) shows a plan view of a multiplex PCR chip 600, FIG. 6(b) shows a cross-sectional view of A-A' direction of the multiplex PCR chip 600, and FIG. 6(c) shows a perspective view of the bottom surface of a portion of the multiplex PCR chip 600 shown in FIGS. 6(a) and 6(b).

In the present invention, the reaction area 224 may include a light measurement area for measuring products of various reactions (e.g., a PCR reaction, a hybridization reaction and the like) performed in the reaction area 224. Here, the light measurement area is at least a partial area in the reaction area 224 in which an optical signal emitted from a reaction product is detected, and the light measurement area may correspond to an area in which a probe 240 showing a result of the hybridization reaction is arranged.

Referring to FIG. 6, the multiplex PCR chip 600 may further include a bubble removing part 610. The bubble removing part 610 is an element for preventing bubbles contained in the fluid from being positioned in a predetermined area in the reaction area (e.g., the probes 240 or the probe fixing part 510), and as shown in the figure, it may be formed to be protruded from the inner surface of the third plate 230 toward the bottom. Specifically, since the bubble removing part 610 is an element formed to be protruded from the bottom inner surface of the third plate 230 toward the inside of the reaction area, the bubbles contained in the fluid are pushed from the bubble removing part 610 to a surrounding area due to buoyancy and arranged in a surrounding space. That is, the bubbles are moved out from the light measurement area to the outside and do not affect sensitivity of the optical signal emitted from the reaction product existing in the light measurement area.

Particularly, as at least a portion of the third plate 230, the bubble removing part 610 may be configured of a light transmissive material, and accordingly, the optical signal generated from the reaction product in the light measurement area may pass through the bubble removing part 610 and flow out to the outside of the multiplex PCR chip 600 without degradation of sensitivity. If the reaction product in the reaction area 224 (i.e., the probes 240) is measured using the multiplex PCR chip 600 like this, sensitivity of the optical signal is considerably enhanced although the multiplex PCR chip 600 is extremely miniaturized since the sensitivity is not affected by the bubbles generated in the reaction area 224, and thus a plurality of small amount reaction products can be simultaneously measured in a speedy and accurate way.

Use of the bubble removing part 610 like this is only exemplary, and the bubble removing part 610 may be utilized for various purposes according to embodiments to which the present invention is applied. For example, the bubble removing part 610 may be used to remove bubbles contained in the fluid from the flow of the fluid while the fluid moves via the reaction area.

In addition, the shape of the bubble removing part 610 shown in FIG. 6 is only exemplary, and the shape is not limited thereto, and according to embodiments of the present invention, the shape may be diversely modified and applied.

Figure 7:
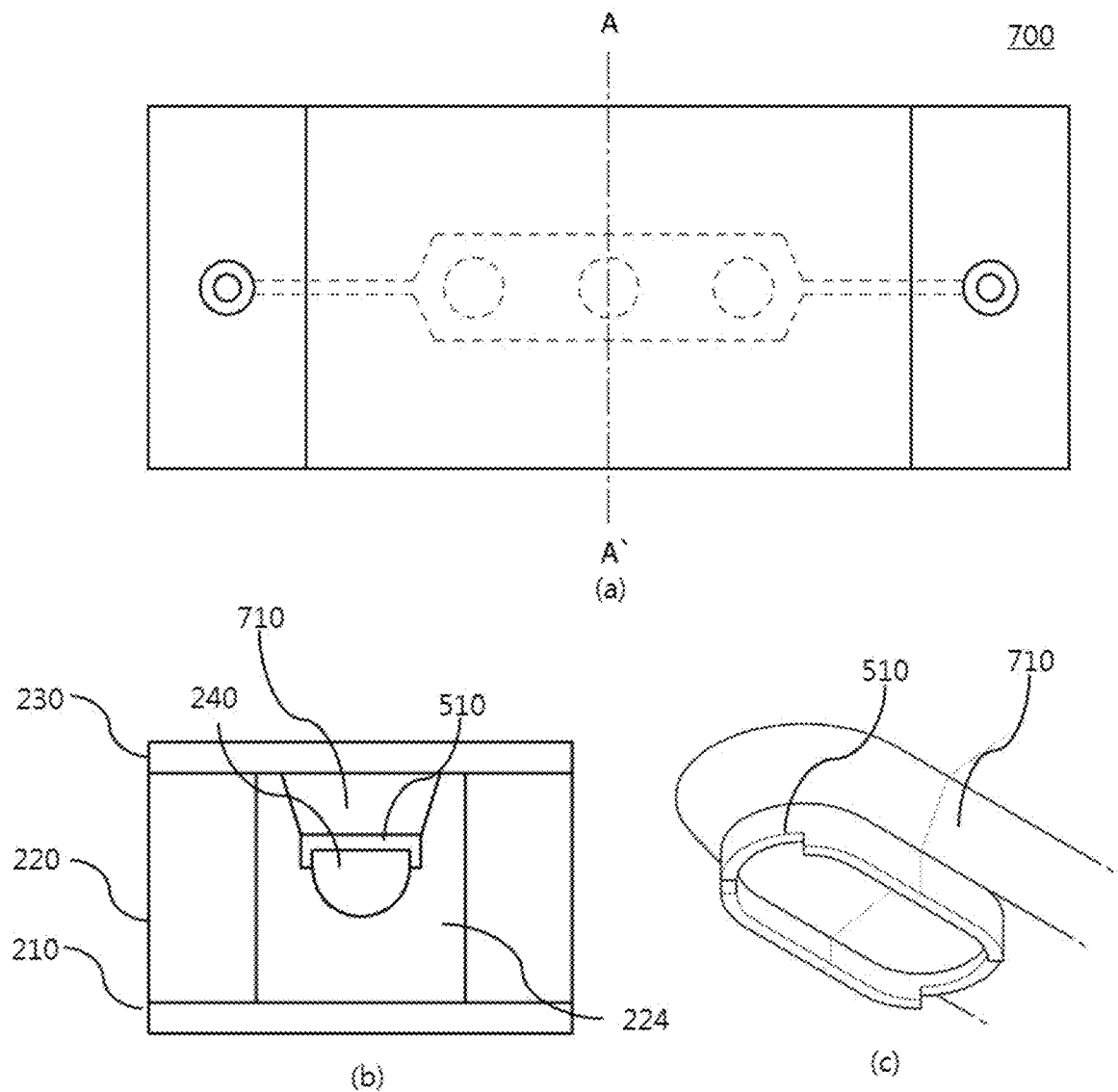
FIG. 7 shows a multiplex PCR device according to an embodiment of the present invention.

FIG. 7 shows a multiplex PCR device according to an embodiment of the present invention.

Specifically, FIG. 7(a) shows a plan view of a multiplex PCR chip 700, FIG. 7(b) shows a cross-sectional view of A-A' direction of the multiplex PCR chip 700, and FIG. 7(c) shows a perspective view of the bottom surface of a portion of the multiplex PCR chip 700 shown in FIGS. 7(a) and 7(b).

Referring to FIG. 7, a bubble removing part 710 may be configured of an inclined surface extended from the bottom inner surface of the third plate 230 to have an inclined surface and connected to the probe fixing part 510. If the side surface of the bubble removing part 710 is configured of an inclined surface like this, since bubbles may move toward the top of the reaction area along the inclined surface, the bubbles may be further easily moved to be arranged in the surrounding space of the bubble removing part 710.

Although it is not shown in FIGS. 6 and 7, according to embodiments, the probe fixing part may be configured of a flat surface provided on the bottom surface of the surrounding part of the probe fixing part and an inclined surface extended from the circumference of the flat surface and connected to the bubble removing part. If the side surface around the probe fixing part is configured of an inclined surface like this, since the bubbles around the probes may easily move to the outside of the light measurement area (to the top of the reaction area) along the inclined surface like the bubble removing part having an inclined surface on the side surface, efficiency of light measurement may be improved further more.

In addition, although it is not shown in FIGS. 6 and 7, according to embodiments, the bubble removing part may further include a bubble collection part formed by depressing the bottom surface of the third plate toward the top along the circumference of the bubble removing part. Since the bubble collection part is positioned at a relatively higher portion of the reaction area compared with the areas other than the bubble collection part, the bubbles pushed from the bubble removing part may be collected in the bubble collection part.

Figure 8:
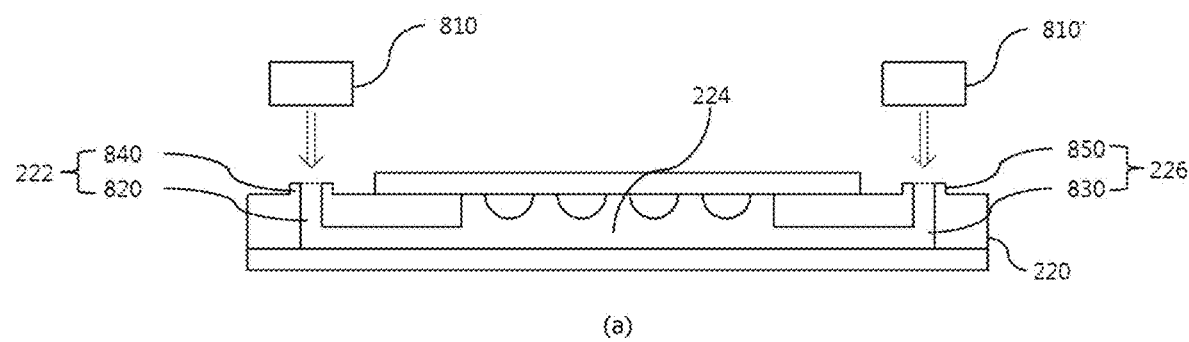
FIG. 8 shows an example of using a multiplex PCR chip according to an embodiment of the present invention.
Figure 8:
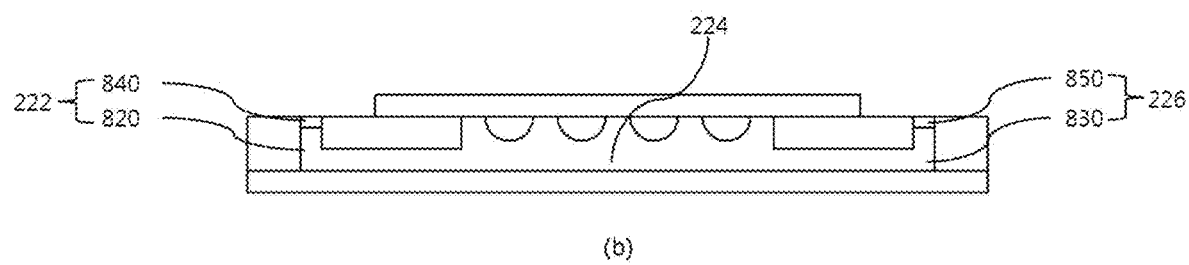

FIG. 8 shows an example of using a multiplex PCR chip according to an embodiment of the present invention.

Referring to FIG. 8, since heaters 810 and 810' are applied to the inflow part 222 and the outflow part 226 of the multiplex PCR chip 200, the inside of the multiplex PCR chip (i.e., the reaction area 224) may be tightly sealed.

More specifically, each of the inflow part 222 and the outflow part 226 of the multiplex PCR chip 200 may include an opening part 820 and 830 formed to penetrate the second plate 220, and a protrusion part 840 and 850 formed to be adjacent to the opening part 820 and 830 by protruding the surface of the second plate 220. That is, since the heaters 810 and 810' are applied to the inflow part 222 and the outflow part 226 of the multiplex PCR chip 200 and transfer heat, the protrusion parts 840 and 850 of the inflow part 222 and the outflow part 226 are melted, and the opening parts 820 and 830 can be tightly sealed. Therefore, after the fluid flows into the reaction area 224 through the inflow part 222, drainage of at least some of the fluid to the outside can be prevented in the process of performing the PCR reaction or the like.

FIGS. 9a to 9d show a heat block according to an embodiment of the present invention.

Figure 9A:
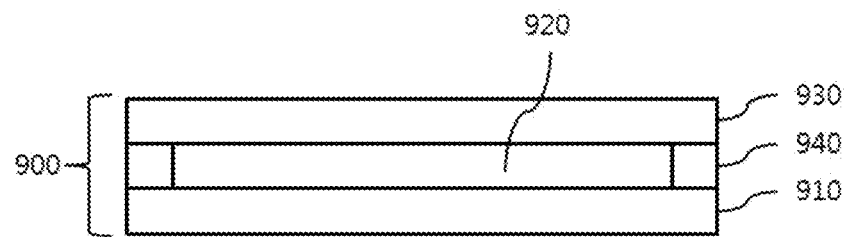
FIGS. 9a to 9d show a heat block according to an embodiment of the present invention.

Referring to FIG. 9a, since at least one heat block 900 contacts with the multiplex PCR chip 200 to 700 according to an embodiment of the present invention, a temperature for performing a denaturing step, an annealing step and an extension (amplification) step for amplifying a nucleic acid molecule can be maintained. Here, the heat block 900 may be provided with a substrate 910, a heat generation layer 920 arranged on the substrate 910, an insulation protection layer 930 arranged on the heat generation layer 920, and an electrode 940 arranged to be connected to the heat generation layer 920.

The substrate 910 is a board of a plastic or metallic material having high heat resistance, and although the substrate 910 is shown in the shape of a plate, it may have various shapes such as a semi-cylindrical shape, a semi-spherical shape and the like. In addition, the substrate 910 may perform a function of supporting the heat generation layer 920.

The heat generation layer 920 may perform a heat source function of the heat block 900 for performing the denaturing step, the annealing step and the extension (amplification) step of the multiplex PCR.

In one embodiment, the heat generation layer 920 may include a heat wire as a heat source. The heat wire may generate heat using the power applied from the electrode 940 and may be operably connected to various temperature sensors (not shown) for monitoring the temperature of the heat wire. The heat wire may be arranged to be symmetrical in the vertical and/or horizontal direction with respect to the center point of the surface of the heat block 900 in order to constantly maintain the overall temperature inside the heat block 900. The heat wire symmetrical in the vertical and/or horizontal direction may be diversely arranged.

In one embodiment, an adhesive force reinforcement layer (not shown) may be formed between the substrate 910 and the heat generation layer 920 to strongly fix the heat generation layer 920 to the substrate 910. The adhesive force reinforcement layer may be formed of silica or polymer.

The insulation protection layer 930 is an element for physically and/or electrically protecting the heat generation layer 920 and may include an insulation material. For example, the insulation material may be selected from a group configured of dielectric oxide, perylene, nano-particles and a polymer film. Meanwhile, the insulation protection layer 930 may be transparent.

The electrode 940 is arranged to be directly or indirectly connected to the heat generation layer 920 and supplies power to the heat generation layer 920. The heat generation layer 920 may be implemented using various materials capable of supplying power and may be implemented using a material selected from a group configured of, for example, a metallic material, a conductive epoxy, a conductive paste, a solder and a conductive film. According to FIG. 9, although the electrode 940 is arranged to be connected to both side surfaces of the heat generation layer 920, it may be arranged to be connected at a diversely operable position if it can supply power to the heat generation layer 920. In addition, the electrode 940 may be included in the multiplex PCR device or electrically connected to a power supply arranged outside. For example, the electrode 940 directly contacts with the heat generation layer 920 and connects the heat generation layer 920 to an external circuit (not shown) through a wire (not shown), and a terminal may be arranged to stably fix the wire to the electrode 940.

The multiplex PCR chip 200 to 700 contacts with at least a partial area on the top surface of the heat block 900 to be heated up or cooled down according to supply or recovery of heat by the heat block 900 and may perform each reaction step of the multiplex PCR. According to embodiments, the multiplex PCR chip 200 to 700 may directly or indirectly contact with the heat block 900 and perform heat supply.

Figure 9B:
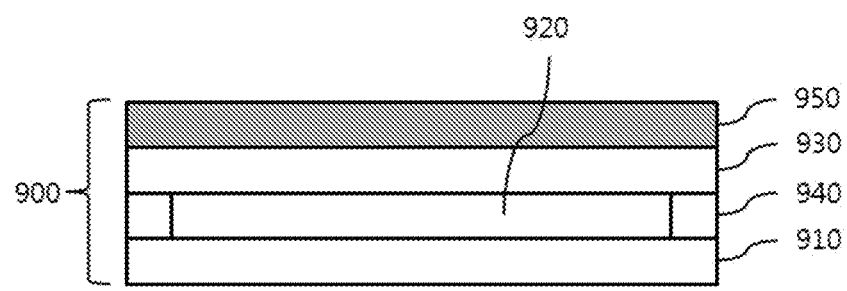

According to FIG. 9b, a light reflection prevention layer 950 is arranged to contact with the top surface of the insulation protection layer 930 to further enhance sensing efficiency. Specifically, the light reflection prevention layer 950 performs an insulation protection function in combination with the insulation protection layer 930 and may include a light reflection prevention material. Here, although the light reflection prevention material may be, for example, a fluoride such as $MgF_2$ or an oxide such as $SiO_2$ or $Al_2O_3$, if a material has a property capable of preventing reflection of light, it can be used without limit.

Figure 9C:
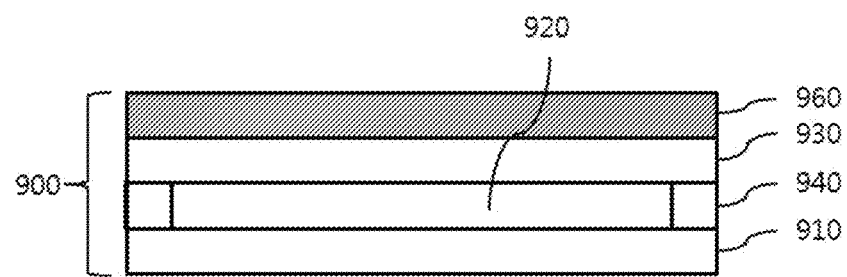

According to FIG. 9c, a light absorption layer 960 is arranged to contact with the top surface of the insulation protection layer 930, and the light absorption layer 960 may include a light absorption material. Here, although the light absorption material may be, for example, mica, if a material has a property capable of absorbing light, it can be used without limit. Accordingly, since the light absorption layer 960 absorbs some of light originated from a light source, generation of reflection light acting as a noise of an optical signal may be suppressed greatly.

Figure 9D:
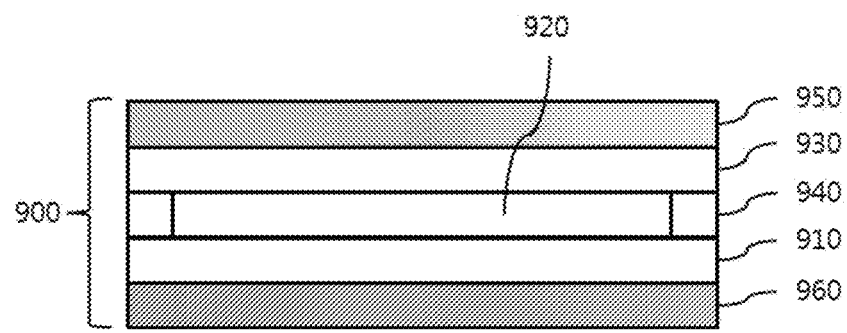

According to FIG. 9d, sensing efficiency can be enhanced further more when the light absorption layer 960 is formed by processing a light absorption material on the bottom surface of the heat block 900 and, at the same time, the light reflection prevention layer 950 is formed by processing a light reflection prevention material on the top surface of the heat block 900. That is, a ratio of optical signal to noise should have a value as high as possible for effective real-time monitoring of the multiplex PCR, and the ratio of optical signal to noise can be increased if a reflection rate of excitation light from the multiplex PCR chip 200 to 700 is low.

The structure and shape of the heat block 900 shown in FIGS. 9a to 9d are only exemplary and may be diversely modified and applied according to embodiments of the present invention. For example, according to embodiments, the order of stacking the constitutional components 910 to 960 configuring the heat block 900 may be changed.

Figure 10:
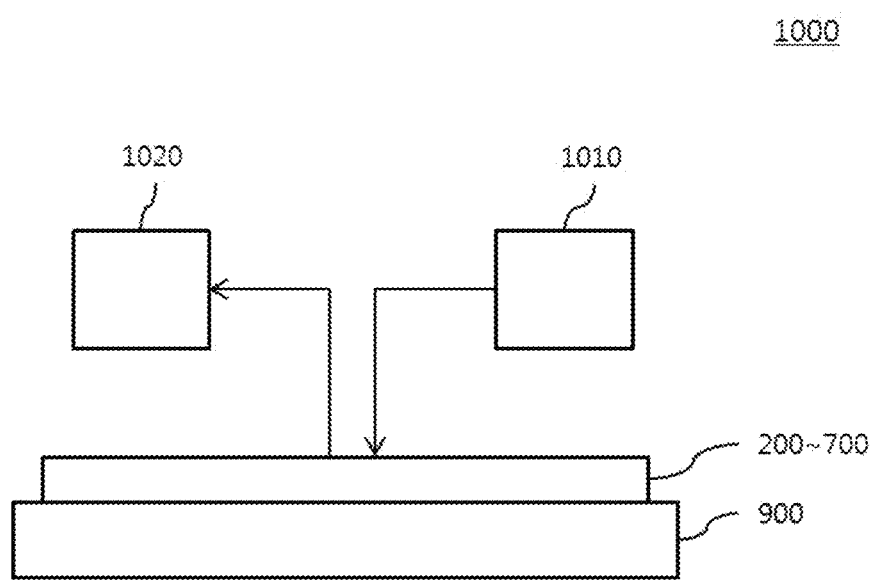
FIG. 10 shows a multiplex PCR device according to an embodiment of the present invention.

FIG. 10 shows a multiplex PCR device according to an embodiment of the present invention.

Referring to FIG. 10, a multiplex PCR device 1000 may further include a heat block 900, a multiplex PCR chip 200 to 700, a light providing part 1010 operably arranged to provide light to the multiplex PCR chip 200 to 700, and a light detection part 1020 operably arranged to receive light emitted from the multiplex PCR chip 200 to 700.

The light providing part 1010 may be a module for providing light to the multiplex PCR chip 200 to 700. In one embodiment, the light providing part 1010 may include a light source for emitting light, such as a light emitting diode (LED) light source, a laser light source or the like, a first optical filter for selecting light having a predetermined wavelength from the light emitted from the light source, and a first optical lens for increasing strength of the emitted light by collecting the light emitted from the first optical filter. According to additional embodiments, the light providing part 1010 may further include a first aspheric lens arranged between the light source and the first optical filter to disperse light. That is, the range of the light emitted from the light source may be extended by adjusting the direction of arranging the first aspheric lens so that the light may arrive at an area capable of measuring the light. However, the configuration of the light providing part 1010 is not limited thereto.

The light detection part 1020 is a module for receiving the light emitted from the multiplex PCR chip 200 to 700 and measuring a product of PCR reaction performed in the multiplex PCR chip 200 to 700. The light emitted from the light providing part 1010 passes through or reflected from the multiplex PCR chip 200 to 700, specifically, the reaction area 224 or the probe 240 of the multiplex PCR chip 200 to 700, and in this case, an optical signal generated by amplification of a nucleic acid may be detected. In one embodiment, the light detection part 1020 may include a second optical lens for increasing strength of the emitted light by collecting the light emitted from the multiplex PCR chip 200 to 700, a second optical filter for selecting light having a predetermined wavelength from the light emitted from the second optical lens, and an optical analyzer for detecting the optical signal from the light emitted from the second optical filter. According to additional embodiments, the light detection part 1020 may further include a second aspheric lens arranged between the second optical filter and the optical analyzer to integrate the light emitted from the second optical filter, and/or a photodiode integrated circuit arranged between the second aspheric lens and the optical analyzer to remove noise of the light emitted from the second aspheric lens and amplify the light emitted from the second aspheric lens.

Although the light providing part 1010 radiates excitation light having one wavelength toward multiple types of probes 240 in the multiplex PCR chip 200 to 700 and generates emission light by the same dyeing sample, i.e., emission light of the same color, sequences of amplified nucleic acid molecules can be distinguished based on positions of the probes 240. Accordingly, the light providing part 1010 may detect a multiplex PCR product using only one type of light source and filter without the need of being provided with multiple types of light sources and filters. In the same manner, the light detection part 1020 may also detect a multiplex PCR product with only one type of filter. Compared with a conventional multiplex PCR device, such a configuration of the light providing part 1010 and the light detection part 1020 may reduce the time consumed for detection, as well as miniaturizing optical equipment and reducing the cost of the equipment.

In addition, whether a target nucleic acid sequence is amplified and a degree of the amplification can be measured and analyzed in real-time by monitoring in real-time a result of the reaction generated by the amplification of the nucleic acid in the reaction area 224, particularly, in the probe 240, while each cyclic step of the multiplex PCR is progressed in the multiplex PCR chip 200 to 700.

Although it is not shown in FIG. 10, according to embodiments, the multiplex PCR device 1000 may further include at least one or more dichroic filters for adjusting a progress direction of the light so that the light emitted from the light providing part 1010 may arrive at the light detection part 1020 and separating light having a predetermined wavelength. Here, the dichroic filter is a module for selectively passing light according to wavelength or selectively reflecting the light at an adjusted angle. For example, a first dichroic filter may be arranged to be inclined at an angle of about 45 degrees with respect to the optical axis of the light emitted from the light providing part 1010 to selectively pass short wavelength components of the light according to wavelength and selectively reflecting long wavelength components of the light at the right angle so that the light may arrive at the multiplex PCR chip 200 to 700. In addition, for example, a second dichroic filter may be arranged to be inclined at an angle of about 45 degrees with respect to the optical axis of the light reflected from the multiplex PCR chip 200 to 700 and the heat block to selectively pass short wavelength components of the light according to wavelength and selectively reflecting long wavelength components of the light at the right angle so that the light may arrive at the light detection part 1020.

In FIG. 10, although it is shown in the figure that the light providing part 1010 and the light detection part 1020 are arranged above the multiplex PCR chip 200 to 700 and the heat block 900 (reflection type), this is only exemplary, and they may be arranged at various positions according to embodiments to which the present invention is applied. For example, the light providing part 1010 and the light detection part 1020 may be arranged above and below the multiplex PCR chip 200 to 700 and the heat block 900 (transmission type).

Figure 11A:
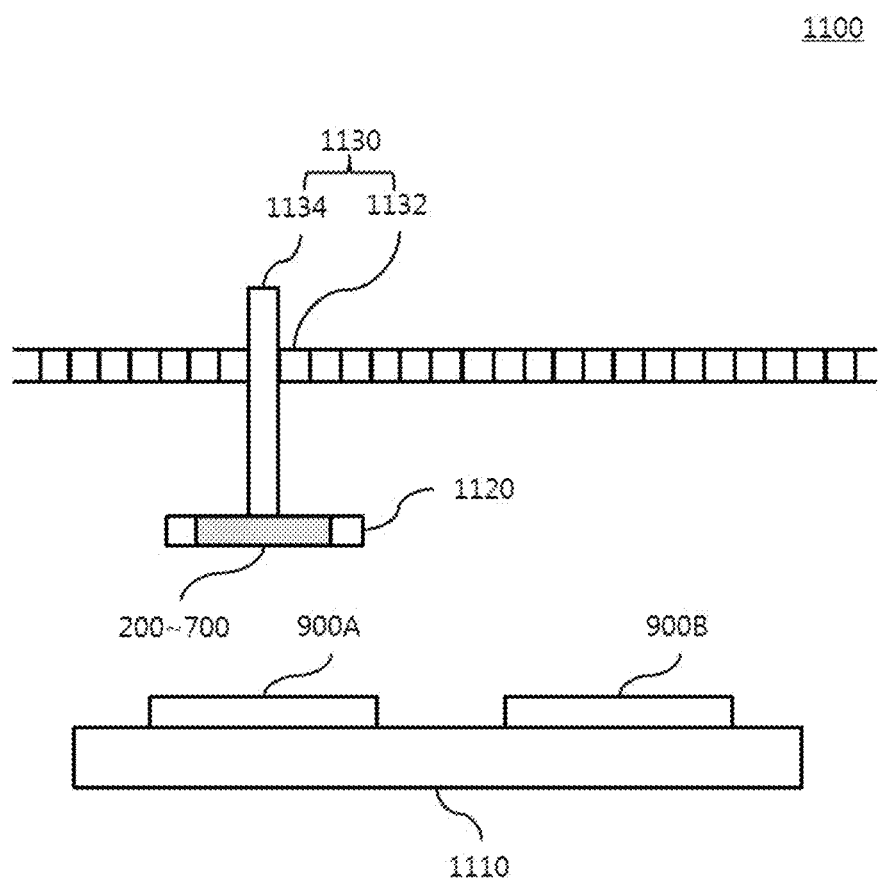
FIGS. 11a and 11b show a multiplex PCR device according to an embodiment of the present invention.
Figure 11B:
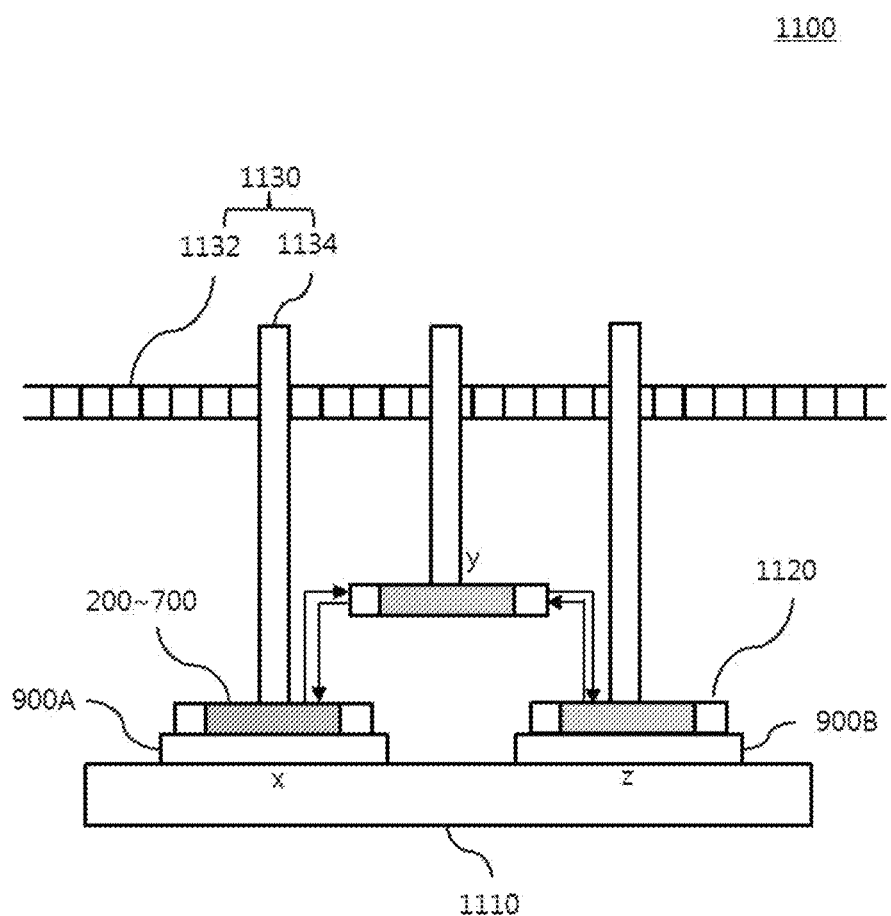

FIGS. 11a and 11b show a multiplex PCR device according to an embodiment of the present invention.

Referring to FIG. 11a, a multiplex PCR device 1100 may include a substrate 1110; a first heat block 900A arranged on the substrate 1110 and a second heat block 900B arranged to be spaced apart from the first heat block 900A; a chip holder 1120 in which a multiplex PCR chip 200 to 700 is installed; and a driving part 1130 for moving the chip holder 1120.

The substrate 1110 may include all materials having a quality which does not change physical and/or chemical properties by heating the first heat block 900A and the second heat block 900B and maintaining the temperature and does not generate heat exchange between the first heat block 900A and the second heat block 900B. For example, the substrate 1110 may include a material such as plastic or the like or may be configured of such a material.

The first heat block 900A and the second heat block 900B are blocks for maintaining a temperature for performing a denaturing step, an annealing step and an extension (amplification) step for amplifying a nucleic acid, and since the heat blocks are described to be the same as the heat block 900 described with reference to FIG. 9, duplicated description will be omitted. Each of the heat blocks 900A and 900B may be implemented to maintain a temperature appropriate for performing the denaturing step, the annealing step and the extension (amplification) step. For example, the heat blocks 900A and 900B may maintain a temperature of 50 to 100° C., and preferably, when the heat blocks 900A and 900B perform the denaturing step, the heat blocks may maintain a temperature of 90 to 100° C., preferably 95° C., and when the heat blocks 900A and 900B perform the annealing and extension (amplification) step, the heat blocks may maintain a temperature of 55 to 75° C., preferably 72° C. However, if a temperature is appropriate to perform the denaturing step or the annealing and extension (amplification) step, it is not limited thereto. The first heat block 900A and the second heat block 900B may be spaced apart from each other by a predetermined distance so that heat exchange may not occur. Accordingly, since the heat exchange does not occur between the first heat block 900A and the second heat block 900B even in the nucleic acid amplification reaction that can be seriously affected by minor temperature change, accurate control of the temperature for the denaturing step and the annealing and extension (amplification) step can be accomplished. In addition, since the first heat block 900A and the second heat block 900B may entirely heat up the surface contacting with the multiplex PCR chip 200 to 700 and maintain the temperature when the multiplex PCR chip 200 to 700 contacts with one side of each heat block 900A and 900B, the fluid in the multiplex PCR chip 200 to 700 may be uniformly heated, and its temperature can be maintained. In a conventional multiplex PCR device using a single heat block, the temperature change rate in the single heat block is accomplished within a range of 3 to 7° C. per second, whereas the multiplex PCR device 1100 includes two heat blocks, and accordingly, the temperature change rate in each of the heat blocks 900A and 900B is accomplished within a range of 20 to 40° C. per second, and thus time of the multiplex PCR reaction can be reduced greatly.

The multiplex PCR chip 200 to 700 may be installed in the chip holder 1120. The inner wall of the chip holder 1120 may have a shape and a structure to fixedly contact with the outer wall of the multiplex PCR chip 200 to 700. In addition, the multiplex PCR chip 200 to 700 may be attached to and detached from the chip holder 1120. The chip holder 1120 may be operably connected to the driving part 1130.

The driving part 1130 may move the chip holder 1120 horizontally and/or vertically onto the heat blocks 900A and 900B. Specifically, the driving part 1130 may include all means capable of moving the chip holder 1120 horizontally and/or vertically onto the first heat block 900A and the second heat block 900B. The chip holder 1120 may perform a reciprocating motion between the first heat block 900A and the second heat block 900B by horizontal movement of the driving part 1130, and the chip holder 1120 may contact with and separate from the first heat block 900A and the second heat block 900B by vertical movement of the driving part 1130. To this end, the driving part 1130 may include a rail 1132 extended in the horizontal direction and a connection member 1134 arranged to be slidingly movable in the horizontal direction through the rail 1132 and slidingly movable in the vertical direction, and the chip holder 1120 may be arranged at one end of the connection member 1134.

Referring to FIG. 11b, the driving part 1130 may perform a PCR reaction while reciprocally moving the multiplex PCR chip 200 to 700 installed in the chip holder 1120 between the first heat block 900A and the second heat block 900B.

First, the first heat block 900A may be heated up to a temperature for the denaturing step, e.g., 90 to 100° C., preferably 95° C., and the temperature is maintained. In addition, the second heat block 900B may be heated up to a temperature for the annealing and extension (amplification) step, e.g., 55 to 75° C., preferably 72° C., and the temperature is maintained.

After or as soon as the multiplex PCR chip 200 to 700 is installed in the chip holder 1120, the connection member 1134 of the driving part 1130 is controlled to move the multiplex PCR chip 200 to 700 downward to contact the chip holder 1120 installed with the multiplex PCR chip 200 to 700 with the first heat block 900A, so that a first denaturing step of the multiplex PCR may be performed (step x).

Subsequently, the connection member 1134 of the driving part 1130 is controlled to move the multiplex PCR chip 200 to 700 upward to separate the chip holder 1120 installed with the multiplex PCR chip 200 to 700 from the first heat block 900A, so that the first denaturing step of the multiplex PCR is completed, and the multiplex PCR chip 200 to 700 may be moved onto the second heat block 900B through the rail 1132 of the driving part 1130 (step y).

Subsequently, the connection member 1134 of the driving part 1130 is controlled to move the multiplex PCR chip 200 to 700 downward to contact the chip holder 1120 installed with the multiplex PCR chip 200 to 700 with the second heat block 900B, so that a first annealing and extension (amplification) step of the multiplex PCR may be performed (step z).

Finally, the connection member 1134 of the driving part 1130 is controlled to move the multiplex PCR chip 200 to 700 upward to separate the chip holder 1120 installed with the multiplex PCR chip 200 to 700 from the second heat block 900B, so that the first annealing and extension (amplification) step of the multiplex PCR is completed, and the nucleic acid amplification reaction can be performed by repeating the x, y and z steps after moving the multiplex PCR chip 200 to 700 onto the first heat block 900A through the rail 1132 of the driving part 1130 (cyclic step).

Figure 12:
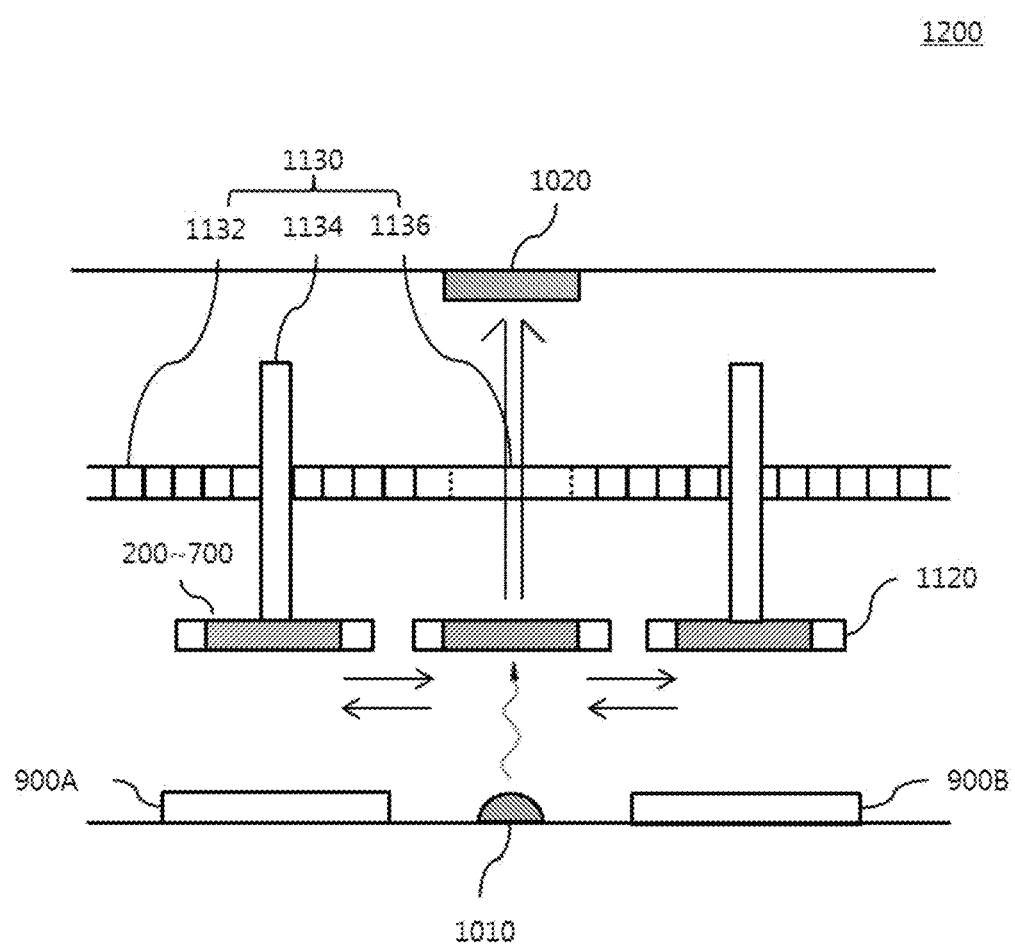
FIG. 12 shows a multiplex PCR device according to an embodiment of the present invention.

FIG. 12 shows a multiplex PCR device according to an embodiment of the present invention.

Referring to FIG. 12, in a multiplex PCR device 1200, a light providing part 1010 and a light detection part 1020 may be arranged with intervention of the first heat block 900A and the second heat block 900B therebetween. A penetration part 1136 for passing light emitted from the light providing part 1010 may be formed in the driving part 1130 to measure the light, and the multiplex PCR chip 200 to 700 may be implemented using a light transmissive material, specifically, a light transmissive plastic material.

A degree of amplification of the nucleic acid in the multiplex PCR chip 200 to 700, among the nucleic acid amplification reaction performed by the multiplex PCR device 1200, may be detected in real-time by the arrangement of the light providing part 1010 and the light detection part 1020 shown in FIG. 12. Specifically, the multiplex PCR chip reciprocates between the first heat block 900A and the second heat block 900B to perform each step of the PCR reaction. In the process, the driving part 1130 may stop the multiplex PCR chip 200 to 700 in a space between the first heat block 900A and the second heat block 900B. At this point, since light is emitted from the light providing part 1010 and the emitted light passes through the multiplex PCR chip 200 to 700, specifically, through the reaction area 224 or the probe 240 of the multiplex PCR chip 200 to 700, the light detection part 1020 may detect an optical signal generated by the amplification of the nucleic acid.

As described above, according to the multiplex PCR device 1200, an amount of a target nucleic acid sequence may be measured and analyzed in real-time by monitoring a result of the reaction generated by the amplification of the nucleic acid in the reaction area 224, particularly, in the probe 240, while each cyclic step of the multiplex PCR reaction is progressed.

Although it is shown in FIG. 12 that the light providing part 1010 is positioned on the bottom and the light detection part 1020 is positioned on the top, this is only exemplary, and the light providing part 1010 may be positioned on the top and the light detection part 1020 may be positioned on the bottom.

Meanwhile, although a multiplex PCR device performing a PCR reaction using two heat blocks 900A and 900B is shown in FIGS. 11a, 11b and 12, this is only exemplary, and the number of heat blocks used to perform the PCR reaction may be variable. For example, only one heat block may be used for one multiplex PCR chip 200 to 700.

Figure 13:
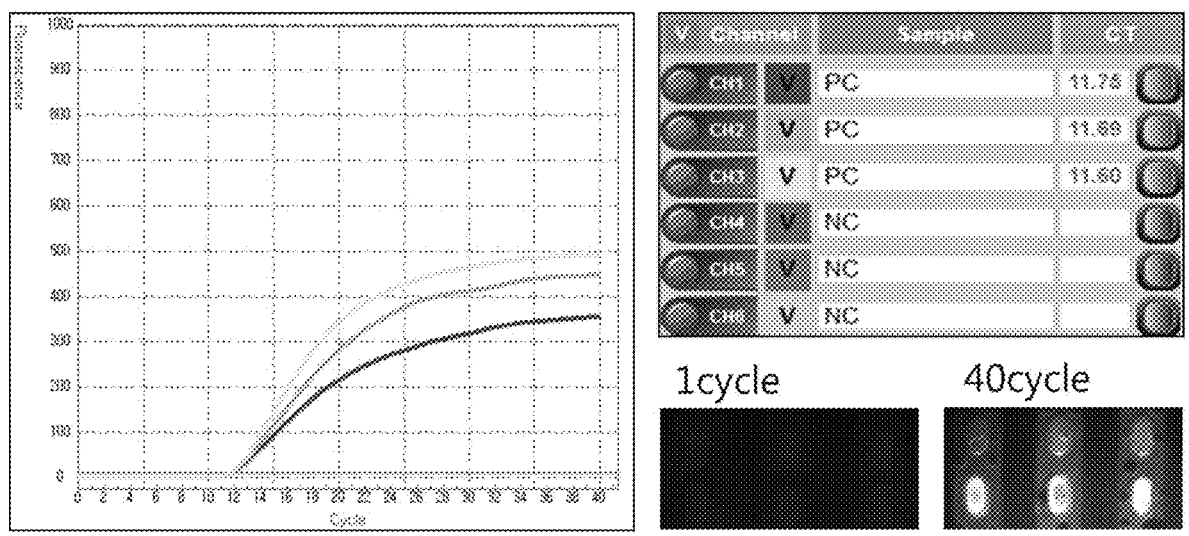
FIG. 13 shows an experiment example of a multiplex PCR device according to an embodiment of the present invention.

FIG. 13 shows an experiment example of a multiplex PCR device according to an embodiment of the present invention.

In the experiment example, PCR is performed and emission light is measured after manufacturing and arranging probes in the multiplex chip to be spaced apart from each other and injecting a PCR reagent that can be detected by the probes.

First, a prepolymer (or hydrogel) solution is prepared by mixing predetermined reagents, and a probe solution is prepared by mixing the prepolymer solution with Yersinia enterocolitica forward primer or the like.

Composition of the reagents of the prepolymer solution is as shown below.

TABLE 1

| Composition | Volume (uL) |
|---|---|
| PEGDA | 200 |
| PEG | 400 |

TABLE 1-continued

| Composition | Volume (uL) |
| --- | --- |
| Darocur 1173 | 50 |
| 3x TE Buffer | 350 |

In addition, composition of the probe solution is as shown below.

TABLE 2

| Composition | Volume (uL) |
| --- | --- |
| Prepolymer solution | 90 |
| *Yersinia enterocolitica* Reverse Primer | 10 |

Subsequently, the probe solution may be cured by radiating ultraviolet rays after being arranged in the multiplex PCR chip. The cured solution is cleansed thereafter using a cleansing liquid. After injecting 20 uL of a PCR reagent containing a reverse primer, which can be complementarily combined with the probes, into the multiplex PCR chip and performing PCR, emission light is measured.

Composition of the PCR reagents is as shown below.

TABLE 3

| Composition | Volume (uL) |
| --- | --- |
| NBS SYBR green 2x master mix | 10 |
| *Yersinia enterocolitica* Reverse Primer | 2 |
| *Yersinia enterocolitica* Template | 1 |
| DW | 7 |

In addition, the driving condition of the PCR is as shown below.

TABLE 4

| PCR steps | Temperature (degrees) | Time (seconds) | Cycle |
| --- | --- | --- | --- |
| Pre-Denaturation | 95 | 60 | 1 |
| Denaturation | 95 | 10 | 40 |
| Annealing | 68 | 10 | |

Referring to FIG. 13, a result of an experiment conducted on the multiplex PCR chip of the present invention according to the condition described above is shown in the figure. As shown in the figure, according to the multiplex PCR chip, sequences of nucleic acid molecules hybridized by probes can be distinguished based on positions of the probes by arranging multiple types of probes specifically hybridized with the sequences of nucleic acid molecules different from each other. This may remove necessity of detecting a PCR product using different fluorescent dyes for marking each of the probes and using a light source and a filter of complex configuration. Accordingly, this may miniaturize optical equipment and reduce the cost of the equipment and, furthermore, improve efficiency of operation of the multiplex PCR device, such as reducing the time consumed for detection.

As described above, the optimum embodiments have been disclosed in the drawings and the specification. Although the specific terms have been used herein, they have been used merely for describing the present disclosure, and have not been used to limit the meanings thereof and the scope of the present disclosure set forth in the claims. Therefore, it will be understood by those having ordinary knowledge in the art that various modifications and other equivalent embodiments can be made. Accordingly, the true technical protection range of this disclosure should be defined by the technical spirit of the attached claims.

The invention claimed is:

1. A multiplex polymerase chain reaction (PCR) chip comprising:
a chamber having a reaction area therein; and
a plurality of probes disposed in the reaction area, each of the plurality of probes being positioned spaced apart from one another,
wherein the each of the plurality of probes has a configuration to be hybridized with each of different amplified sequences of a plurality of nucleic acid molecules, respectively,
wherein the probes are marked with the same fluorescent dye having a same color and arranged on a top surface of the reaction area, wherein each of the different amplified sequences of the plurality of nucleic acid molecules is distinguished based on positions of the probes by detecting light passing through the probes,
wherein the chamber comprises:
a first plate in a plate shape;
a second plate arranged on the first plate to include an inflow part, the reaction area, and an outflow part;
a third plate arranged on the second plate to cover the reaction area, in which the plurality of probes are arranged on an inner surface; and
a plurality of probe fixing parts extending in a direction toward the first plate,
wherein the multiple PCR chip further comprises a bubble removing part, made of a light transmissive material, and protruded from the inner surface of the third plate in a direction toward the first plate to guide bubbles in the reaction area away from the plurality of probes, which are disposed on the bubble removing part, and
wherein each of the plurality of probe fixing parts comprises:
a center part on the bubble removing part accommodating one of the plurality of probes; and
a surrounding part protruded from the center part adjacent to and surrounding the center part.

2. The multiplex PCR chip of claim 1, wherein the porous structure is comprised of at least one of hydrogel, agarose, and paraffin.

3. The multiplex PCR chip of claim 1, wherein the plurality of probes are arranged on a first inner surface of the chamber.

4. The multiplex PCR chip of claim 1, wherein the first plate is comprised of a thermoplastic resin material or a thermosetting resin material selected from a group consisting of polymethylmethacrylate (PMMA), polycarbonate (PC), cycloolefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and a combination thereof, and each of the second plate and the third plate is comprised of a material selected from a group consisting of polydimethylsiloxane (PDMS), cycle olefin copolymer (COC), polymethylmetharcylate (PMMA), polycarbonate (PC), polypropylene carbonate (PPC), polyether sulfone (PES), polyethylene terephthalate (PET), and a combination thereof.

5. The multiplex PCR chip of claim 1, wherein at least a part of the reaction area is defined on the second plate by a penetrated area in a thickness direction, and the third plate is protruded toward the penetrated area.

6. The multiplex PCR chip of claim 1, wherein each of the inflow part and the outflow part has an opening part penetrating both of the second plate and the third plate, and has a protrusion part protruded around the opening part, wherein the protrusion part has a configuration to melt and seal the opening part by heat.

7. A multiplex PCR device comprising:
a multiplex polymerase chain reaction (PCR) chip comprising:
  a chamber having a reaction area therein; and
  a plurality of probes disposed in the reaction area, each of the plurality of probes being positioned spaced apart from one another,
  wherein the each of the plurality of probes has a configuration to be hybridized with each of different amplified sequences of a plurality of nucleic acid molecules, respectively,
  wherein the plurality of probes are marked with the same fluorescent dye having a same color and arranged on a top surface of the reaction area, wherein each of the different amplified sequences of the plurality of nucleic acid molecules is distinguished based on positions of the probes by detecting light passing through the probes,
  wherein the chamber comprises:
  a first plate in a plate shape;
  a second plate arranged on the first plate to include an inflow part, the reaction area, and an outflow part;
  a third plate arranged on the second plate to cover the reaction area, in which the plurality of probes are arranged on an inner surface; and
  a plurality of probe fixing parts extending in a direction toward the first plate,
  wherein the multiple PCR chip further comprises a bubble removing part, made of a light transmissive material, and protruded from the inner surface of the third plate in a direction toward the first plate to guide bubbles in the reaction area away from the plurality of probes, which are disposed on the bubble removing part, and
  wherein each of the plurality of probe fixing parts comprises:
  a center part on the bubble removing part accommodating one of the plurality of probes; and
  a surrounding part protruded from the center part adjacent to and surrounding the center part;
a light providing part radiating an excitation light toward the plurality of probes in the multiplex PCR chip; and
a light detection part detecting an emission light generated from the plurality of probes by the excitation light,
wherein the light providing part and the light detection part use a single wavelength light for a detection.

8. A multiplex PCR device comprising:
a multiplex polymerase chain reaction (PCR) chip comprising:
  a chamber having a reaction area therein; and
  a plurality of probes disposed in the reaction area, each of the plurality of probes being positioned spaced apart from one another,
  wherein the each of the plurality of probes has a configuration to be hybridized with each of different amplified sequences of a plurality of nucleic acid molecules, respectively,
  wherein the plurality of probes are marked with the same fluorescent dye having a same color and arranged on a top surface of the reaction area, wherein each of the different amplified sequences of the plurality of nucleic acid molecules is distinguished based on positions of the probes by detecting light passing through the probes,
  wherein the chamber comprises:
  a first plate in a plate shape;
  a second plate arranged on the first plate to include an inflow part, the reaction area, and an outflow part;
  a third plate arranged on the second plate to cover the reaction area, in which the plurality of probes are arranged on an inner surface; and
  a plurality of probe fixing parts extending in a direction toward the first plate,
  wherein the multiple PCR chip further comprises a bubble removing part, made of a light transmissive material, and protruded from the inner surface of the third plate in a direction toward the first plate to guide bubbles in the reaction area away from the plurality of probes, which are disposed on the bubble removing part, and
  wherein each of the plurality of probe fixing parts comprises:
  a center part on the bubble removing part accommodating one of the plurality of probes; and
  a surrounding part protruded from the center part adjacent to and surrounding the center part; and
at least one heat block contacting with the multiplex PCR chip and provide heat to the multiplex PCR chip.

9. The multiplex PCR device of claim 8, further comprising:
a chip holder in which the multiplex PCR chip is accommodated; and
a driving part horizontally and vertically moving the chip holder onto the heat block,
wherein the heat block includes a first heat block and a second heat block.

10. The multiplex PCR device of claim 9, wherein one heat block of the first heat block and the second heat block has a configuration to maintain a temperature of a denaturing step of a PCR reaction, and the other heat block has a configuration to maintain a temperature of annealing and extension (amplification) steps of the PCR reaction.

11. The multiplex PCR device of claim 9, wherein the first heat block and the second heat block are arranged to be spaced apart from each other to avoid heat exchange therebetween.

12. The multiplex PCR device of claim 9, wherein the driving part includes:
a rail extended in a horizontal direction; and
a connection member sliding along the rail in the horizontal direction and extending in a vertical direction,
wherein the chip holder is located at one end of the connection member.

* * * * *